(12) United States Patent
Shoji et al.

(10) Patent No.: US 6,552,553 B2
(45) Date of Patent: Apr. 22, 2003

(54) BIOELECTRICAL IMPEDANCE MEASURING APPARATUS

(75) Inventors: Tamaki Shoji, Asaka (JP); Fumie Shibata, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/943,266

(22) Filed: Aug. 31, 2001

(65) Prior Publication Data

US 2002/0027439 A1 Mar. 7, 2002

(30) Foreign Application Priority Data

Sep. 1, 2000 (JP) ........................................ 2000-265504

(51) Int. Cl.⁷ ............................................... G01R 27/08
(52) U.S. Cl. ......................... 324/692; 324/715; 600/547
(58) Field of Search ................................. 324/692, 715; 600/547, 393, 372, 382

(56) References Cited

U.S. PATENT DOCUMENTS 5,415,176 A * 5/1995 Sato ........................... 600/547

2002/0040195 A1 * 4/2002 Takehara .................... 600/547
2002/0062090 A1 * 5/2002 Chai .......................... 600/547
2002/0072687 A1 * 6/2002 Hakomori .................. 600/547

FOREIGN PATENT DOCUMENTS

| EP | 0545014 B1 | 8/1997 |
| EP | 1 063 500 | * 12/2000 |
| JP | 11-244252 | * 9/1999 |
| JP | 2000-175878 | 6/2000 |

* cited by examiner

Primary Examiner—Christine Oda
(74) Attorney, Agent, or Firm—McDermott, Will & Emery

(57) ABSTRACT

A bioelectrical impedance measuring apparatus is provided, which includes a measurement board and two pairs of electrodes arranged on the measurement board. A bioelectrical impedance of a subject is detected bringing both foot soles of the subject into contact with the electrodes. Each of the two pairs of electrodes extends approximately radially from the center of the measurement board.

9 Claims, 6 Drawing Sheets

BIOELECTRICAL IMPEDANCE MEASURING APPARATUS

FIELD OF THE INVENTION

The present invention relates to a bioelectrical impedance measuring apparatus for measuring an electrical impedance of a human body by use of four electrodes to determine a body fat ratio, body water, blood pressure or the like.

BACKGROUND OF THE INVENTION

In a conventional body fat scale with a body weight scale for measuring a bioelectrical impedance by use of four electrodes to calculate a body fat ratio and others (hereinafter referred to as "body fat scale"), the four electrodes A1, B1, C1 and D1 are arranged on a cover 100a of the main body 100 of the body fat scale, as shown in FIG. 9. Upon superimposing both foot soles of a subject on the electrodes A1, B1, C1 and D1, the bioelectrical impedance is measured and then the measured body weight, body fat ratio and others are displayed on a display 101.

In order to suppress undesirable influences of differences among subjects, such as differences between adults and children or differences in foot size, the electrodes A1, B1, C1 and D1 of the conventional body fat scale have been designed in large. This has led to increased cost of components and uncomfortable chilly feeling from foot soles superimposed on such electrodes.

SUMMARY OF THE INVENTION

It is an object of the present invention to provide a bioelectrical impedance measuring apparatus capable of solving the aforementioned problems.

In order to achieve this object, according to a first aspect of the present invention, there is provided a bioelectrical impedance measuring apparatus including a measurement board and two pairs of electrodes arranged on the measurement board, wherein a bioelectrical impedance of a subject is detected with bringing both foot soles of the subject into contact with the electrodes, characterized in that each of the two pairs of electrodes is arranged to extend approximately radially from the center of the measurement board.

In the first aspect of the present invention, the two pairs of electrodes may comprise a first pair of adjacent electrodes and a second pair of adjacent electrodes. In this case, each of the first pair of adjacent electrodes may serve as a current supply electrode, and the distance between respective lower portions of the first pair of adjacent electrodes may be less than the distance between respective upper portions of the first pair of adjacent electrodes. Further, each of the second pair of adjacent electrodes may serve as a voltage measuring electrode, and the distance between respective upper portions of the second pair of adjacent electrodes may be less than the distance between respective lower portions of the second pair of adjacent electrodes. Preferably, positioning means for positioning a heel of the subject may be provided near each of the second pair of adjacent electrodes serving as a voltage measuring electrode.

According to a second aspect of the present invention, there is provided a bioelectrical impedance measuring apparatus including a measurement board and two pairs of electrodes arranged on the measurement board, wherein a bioelectrical impedance of a subject is detected with bringing both foot soles of the subject into contact with the electrodes, characterized in that the two pairs of electrodes are arranged to surround the center of the measurement board.

In the second aspect of the present invention, the two pairs of electrodes may comprise a first pair of adjacent electrodes and a second pair of adjacent electrodes. In this case, each of the first pair of adjacent electrodes may serve as a current supply electrode, and the distance between respective lower portions of the first pair of adjacent electrodes may be greater than the distance between respective upper portions of the first pair of adjacent electrodes. Further, each of the second pair of adjacent electrodes may serve as a voltage measuring electrode, and the distance between respective upper portions of the second pair of adjacent electrodes may be greater than the distance between respective lower portions of the second pair of adjacent electrodes. Preferably, positioning means for positioning a heel of the subject may be provided near each of the second pair of adjacent electrodes serving as a voltage measuring electrode.

In one embodiment, convex positioning means may be provided near each of the first pair of adjacent electrodes serving as a current supply electrode.

DETAILED DESCRIPTION OF THE PREFERRED EMBODIMENTS

Figure 1:
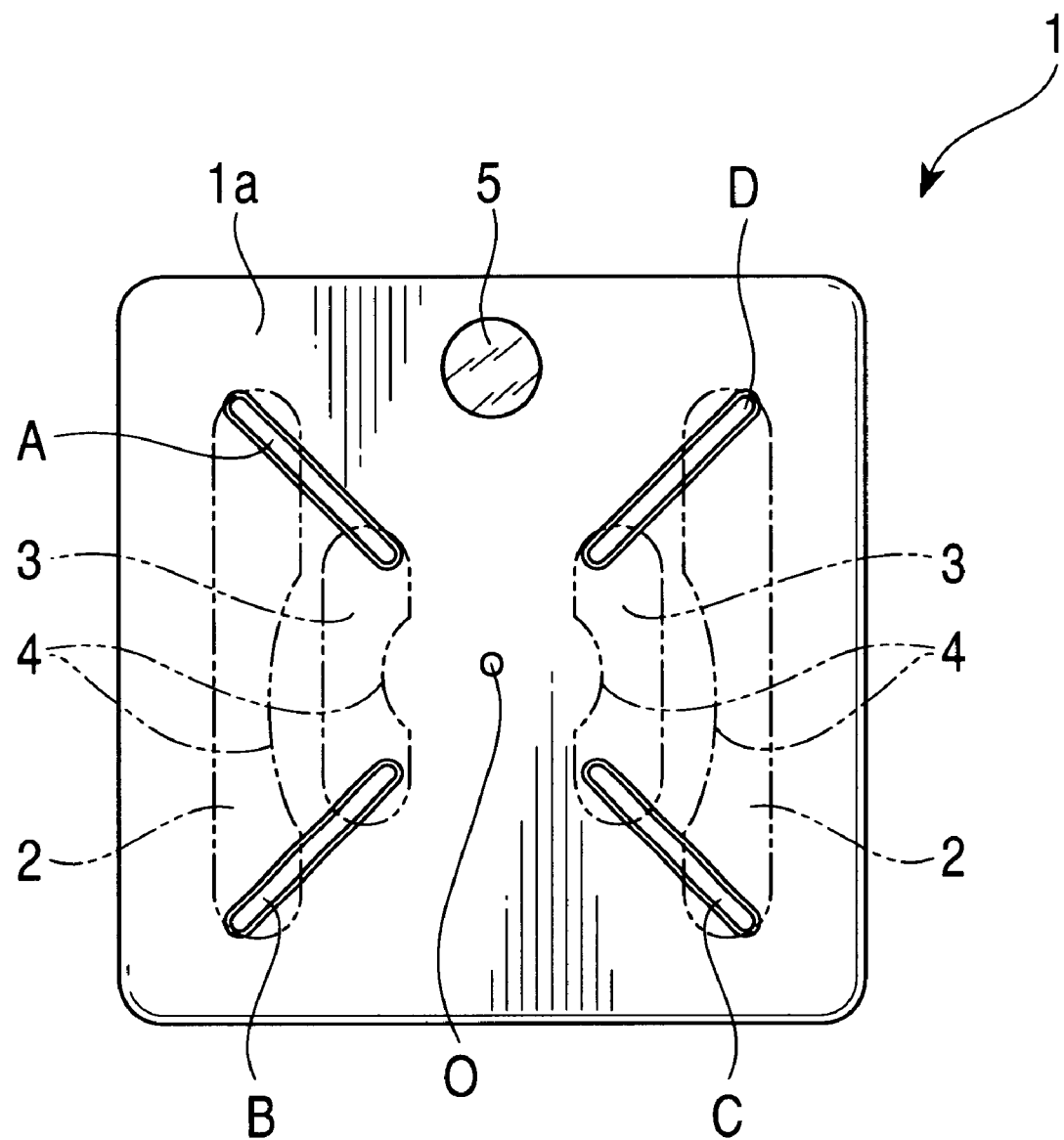
FIG. 1 is a plan view of a body fat scale showing a first embodiment of the present invention.

A first embodiment of the present invention will now be described with reference to the drawings. FIG. 1 is a plan view of a measurement board 1 of a body fat scale implementing the present invention. The measurement board 1 will be paired up with a display section shown in FIGS. 3 to 5 to form the body fat scale. This measurement board 1 is a body fat scale with a body weight scale, and comprises a base (not shown), and a cover 1a. The base houses various conventional mechanisms, such as a weighting mechanism, power supply, control circuit and others, and the cover 1a covers the base.

Figure 2:
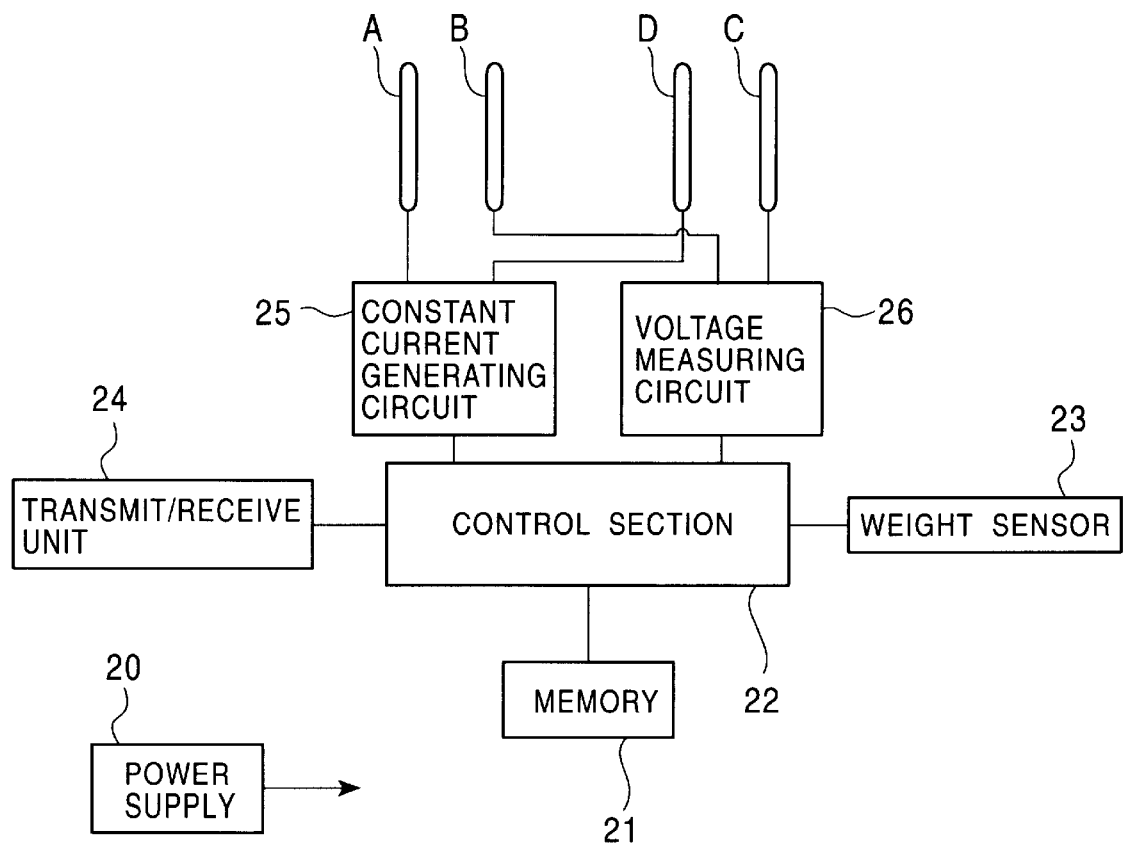
FIG. 2 is a block diagram of a control circuit of the present invention.

Four electrodes are indicated by reference marks A, B, C, and D, and are arranged to make two pairs. Each of one pair of electrodes A and D is connected to a constant current generating circuit 25 to serve as a current supply electrode. Each of the other pair of electrodes B and C is connected to a voltage measuring circuit 26 to serve as a voltage measuring electrode (FIG. 2).

Each of the four electrodes is formed of a conductive material, and has an elongated shape and a small area. Each of the four electrodes is arranged to extend approximately radially from a position spaced by a given distance from the center O of the measurement board 1. In the figure, the distance between respective upper portions of the one pair of electrodes A and D is arranged to be greater than the distance between respective lower portions of the one pair of electrodes A and D, and the distance between respective upper portions of the other pair of electrodes B and C is arranged to be less than the distance between respective lower portions of the other pair of electrodes B and C (FIG. 1).

The reference number 2 indicates a foot position in a bioelectrical impedance measurement for a subject having a relatively large foot size, and the reference number 3 indicates a foot position in the bioelectrical impedance measurement for a subject having a relatively small foot size. Each fallen portion 4 in the foot positions 2 and 3 corresponds to an arch of the foot.

The reference number 5 indicates a communication window. The communication window 5 is provided in the cover 1a of the measurement board 1 to transmit and receive various data, such as a measured body weight, body fat ratio and others, (hereinafter referred to as "data") through any conventional communication means, such as an infrared data communication. In this case, any suitable wire communication may be used as the communication means.

FIG. 2 is a block diagram of a control circuit of the measurement board 1 shown in FIG. 1. A power supply circuit 20 is connected to a control section 22 having a microprocessor, memory 21 and others therein. The control section 22 is connected with a weight sensor 23 for electrically converting weight or the like, and with an infrared ray transmit/receive unit 24 for communicating the data with the display section shown in FIGS. 3 to 5.

As described above, the four electrodes A, B, C and D are paired up in one pair of electrodes A and D connected to the constant current generating circuit 25 and the other pair of electrodes B and C connected to the voltage measuring circuit 26.

The control section 22 is connected with the constant current generating circuit 25 and the voltage measuring circuit 26 which are connected to the four electrodes.

Figure 3:
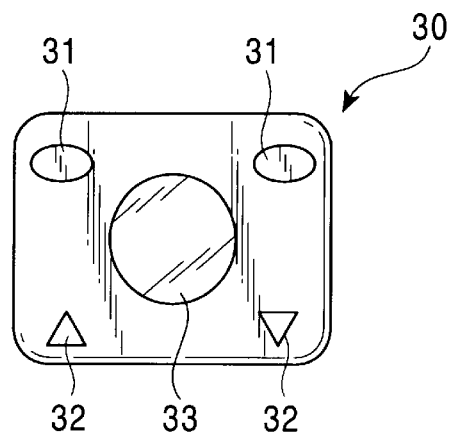
FIG. 3 is a front view of a main body of a display section of the present invention.

FIG. 3 is a front view of the main body 30 of the display section. The reference number 31 indicates a select button for selecting sexuality, height, adult/child or the like. The reference number 32 indicates an up or down button for setting the aforementioned sexuality, height, adult/child or the like, as an operation button provided on the front face of the main body 30 of the display section.

A display window 33 is composed of a LCD window or the like to display various values of body fat ratio, body weight and others. The display window 33 is located at the center of the main body 30 of the display section.

Figure 4:
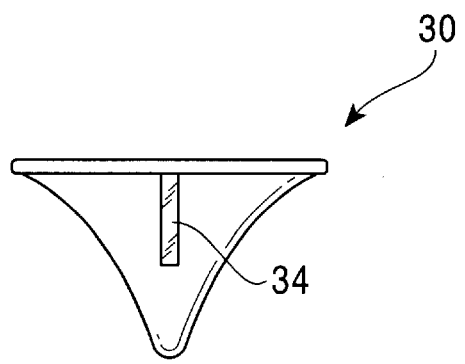
FIG. 4 is a bottom view of the main body of the display section of the present invention.

FIG. 4 is a bottom view of the main body 30 of the display section. A transmit/receive window 34 is provided in the side surface of the main body 30 to receive the information transmitted from the communication window 5 shown in FIG. 1 with infrared rays and to transmit the information to the communication window 5 of the measurement board 1 with infrared rays.

Figure 5:
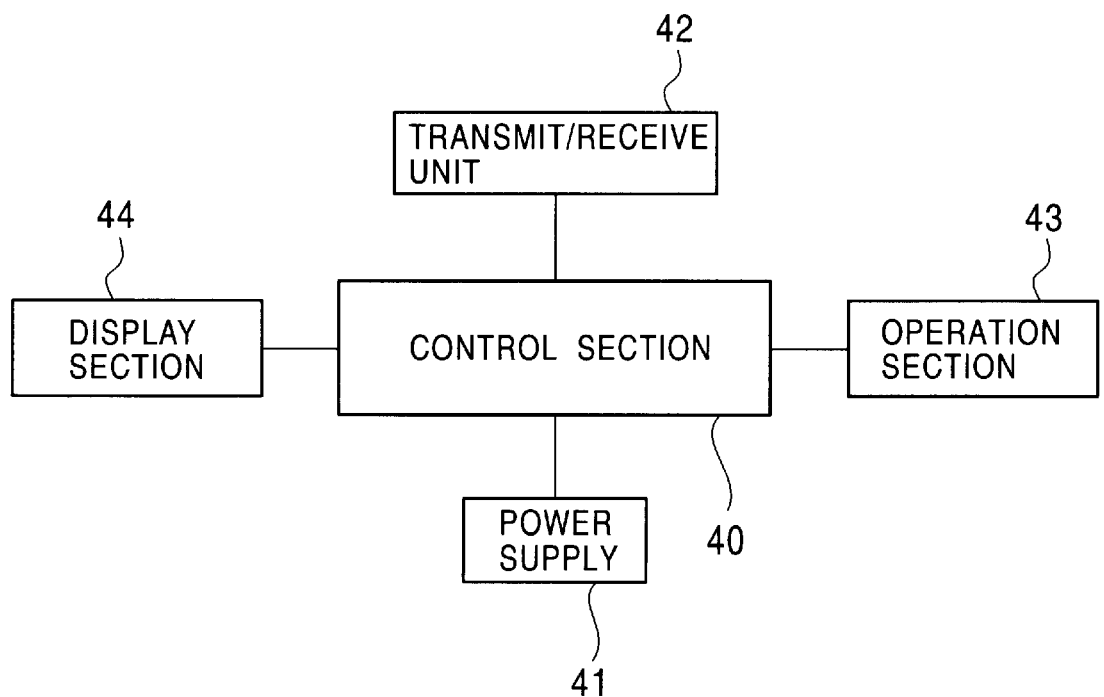
FIG. 5 is a block diagram of a control circuit of the main body of the display section of the present invention.

FIG. 5 is a block diagram of a control circuit of the main body 30 of the. display section. A control section 40 is connected with a power supply 41, an infrared transmit/receive unit 42 for transmitting and receiving the data, an operation section 43 composed of the above operation button or the like, and a display section 44.

Based on the above construction, an operation of each embodiment will now be described.

First, a series of operations concerning the first embodiment will be described. For initiating the measurement, the respective power supplies 41 and 20 of the body fat scale and the main body 30 of the display section are turned on. Then, the select buttons 31 and the operation buttons 32 on the operation section 43 are operated to set the sexuality, height, adult/child and others of a subject. Then, the subject steps with his/her bare feet on the cover 1a (the measurement board 1) forming the body fat scale. In this moment, a subject having a relatively large foot size superimposes his/her foot soles on respective outside positions of the electrodes A, B, C and D with directing his/her toes upward in the figure, or otherwise a subject having a relatively small foot size superimposes his/her foot soles on respective inside positions of the electrodes A, B, C and D with directing his/her toes upward in the figure. This enables any subjects having different foot sizes to bring their foot soles into adequate contact with the electrodes A, B, C and D. Then, a bioelectrical impedance of the subject is measured by these electrodes, and a body weight of the subject is detected by the weight sensor 23. Then, the measured bioelectrical impedance, body weight and other values are converted into a body fat ratio by the control section 22, and this data are transmitted and received by the transmit/receive unit 24. The transmit/receive unit 42 of the main body 30 of the display section receives the data, and the received body weight and body fat ratio are displayed on the display window 33 of the main body 30 of the display section 44. Since each step of this measurement is known from body fat scales which have already been placed on the market, the detailed description will be omitted.

Figure 6:
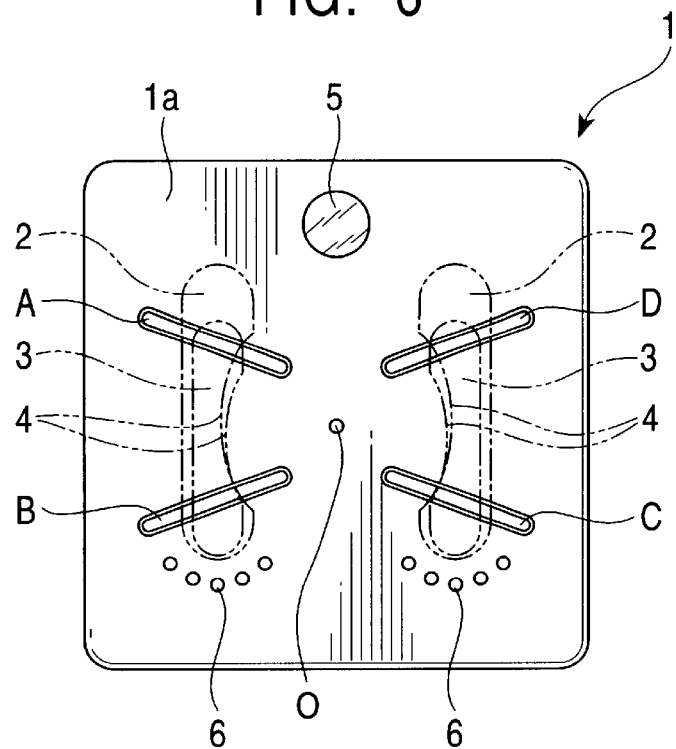
FIG. 6 is a plan view of a body fat scale showing a second embodiment of the present invention.

Next, a second embodiment will be described with reference to FIG. 6. While four electrodes A, B, C, and D are arranged on the measurement board 1 to extend radially from the center O of the measurement board 1 as with the electrodes in FIG. 1, each radial angle of the electrodes or the angle between each of the electrodes and a horizontal line passing through the center of the measurement board 1 is set in smaller than that in each of the electrodes in FIG. 1. In FIG. 6, the distance between respective upper portions of the one pair of electrodes A and D is arranged to be greater than the distance between respective lower portions of the one pair of electrodes A and D, and the distance between respective upper portions of the other pair of electrodes B and C is arranged to be less than the distance between respective lower portions of the other pair of electrodes B and C. Further, a positioning guide 6 is provided on the measurement board near and under each of the electrodes B and C serving as a voltage measuring electrode by attaching a seal or printing. In the measurement according to this embodiment, the select and operation buttons are operated to set the necessary parameters as with the operation in the first embodiment. Then, a subject steps on the measurement board 1 to superimpose his/her foot soles on the electrodes with matching his/her heels with to the positioning guides whether the subject has a large foot size 2 or a small foot size 3. The body weight and body fat ratio are then displayed on the display window 33 of the main body 30 of the display section. Thus, the heels are always placed in a constant position so that the influence of deviations in foot position on the bioelectrical impedance measurement can be prevented to provide a precise measurement. In this case, since a subject having a large foot size contacts the electrodes with his/her soles outside the arches, the sufficient contact between the soles to be measured and the electrodes can be assured.

Figure 7:
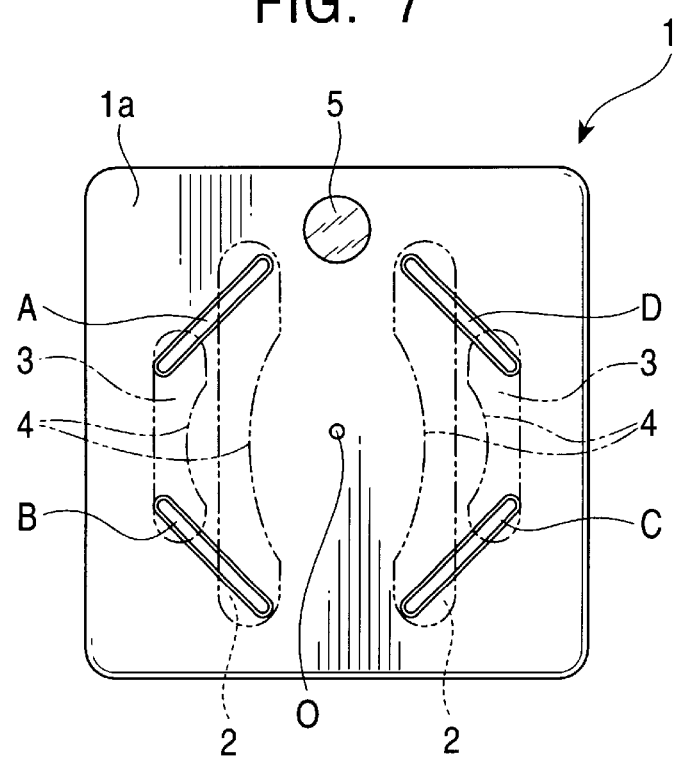
FIG. 7 is a plan view of a body fat scale showing a third embodiment of the present invention.

In a third embodiment shown in FIG. 7, the two pairs of electrodes shown in FIG. 1 are arranged on the measurement board 1 to surround the center O of the measurement board 1. In FIG. 7, the distance between respective upper portions of the one pair of electrodes A and D is arranged to be less than the distance between respective lower portions of the one pair of electrodes A and D, and the distance between respective upper portions of the other pair of electrodes B and C is arranged to be greater than the distance between respective lower portions of the other pair of electrodes B and C. In the measurement of this embodiment, contrary to the first embodiment in FIG. 1, a subject having a large foot size 2 superimposes his/her foot soles on respective inside portion of the electrodes A, B, C, and D, or otherwise a subject having a small foot size 3 superimposes his/her foot soles on respective outside portions of the electrodes A, B, C, and D. Then, the measured body weight and body fat ratio are displayed on the display window 33 of the main body 30 of the display section as with the above embodiments.

Figure 8:
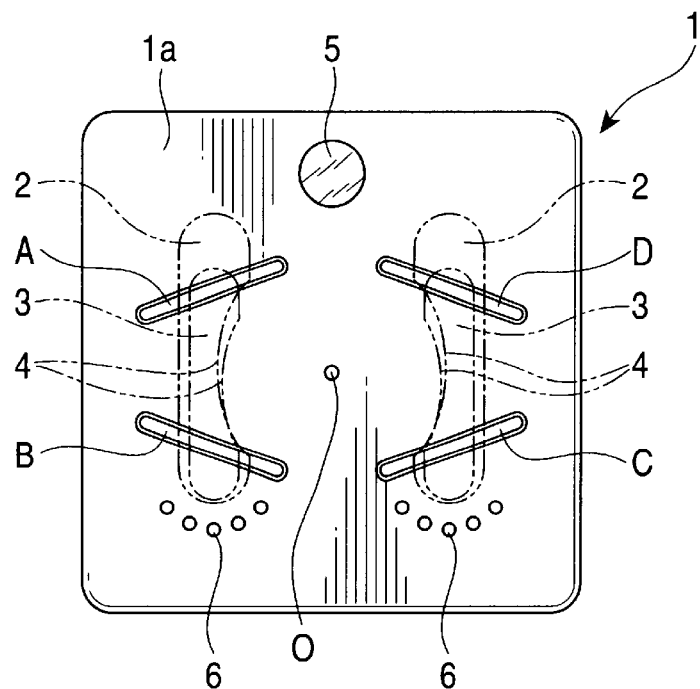
FIG. 8 is a plan view of a body fat scale showing a fourth embodiment of the present invention.
Figure 9:
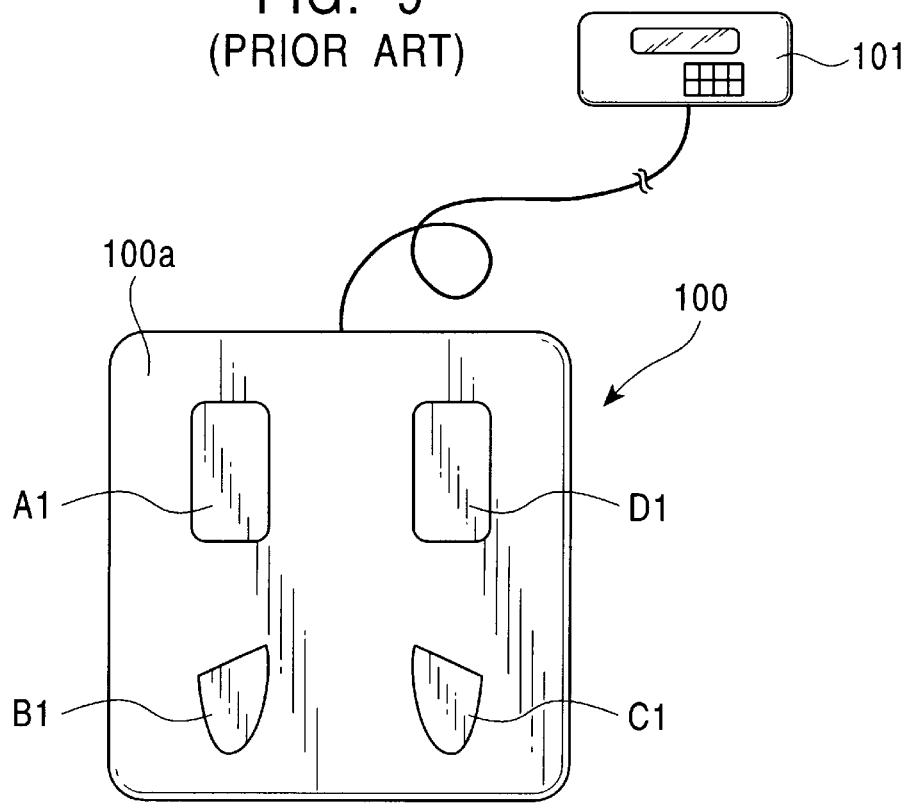
FIG. 9 is a plan view of a conventional body fat scale.

In a fourth embodiment shown in FIG. 8, while two pairs of electrodes are arranged to surround the center O of the measurement board 1 as with the electrode shown in FIG. 7, the angle between each of the electrodes and a horizontal line passing through the center of the measurement board 1 is set in smaller than that in each of the electrodes in FIG. 7. In FIG. 8, the distance between respective upper portions of the one pair of electrodes A and D is arranged to be less than the distance between respective lower portions of the one pair of electrodes A and D, and the distance between respective upper portions of the other pair of electrodes B and C is arranged to be greater than the distance between respective lower portions of the other pair of electrodes B and C. Further, a positioning guide 6 is provided on the measurement board near and under each of the electrodes B and C by attaching a seal or printing. In the measurement according to this embodiment, the select and operation buttons are operated to set the necessary parameters as with the operation in the above embodiments. Then, a subject steps on the measurement board 1 to superimpose his/her foot soles on the electrodes with matching his/her heels with to the positioning guides whether the subject has a large foot size 2 or a small foot size 3. The body weight and body fat ratio are then displayed on the display window 33 of the main body 30 of the display section. Thus, as with the second embodiment, the heels are always placed in a constant position so that the influence of deviations in foot position on the bioelectrical impedance measurement can be prevented to provide a precise measurement. In this case, since a subject having a large foot size contacts the electrodes with his/her soles outside the arches, the sufficient contact between the soles to be measured and the electrodes can be assured.

Figure 10:
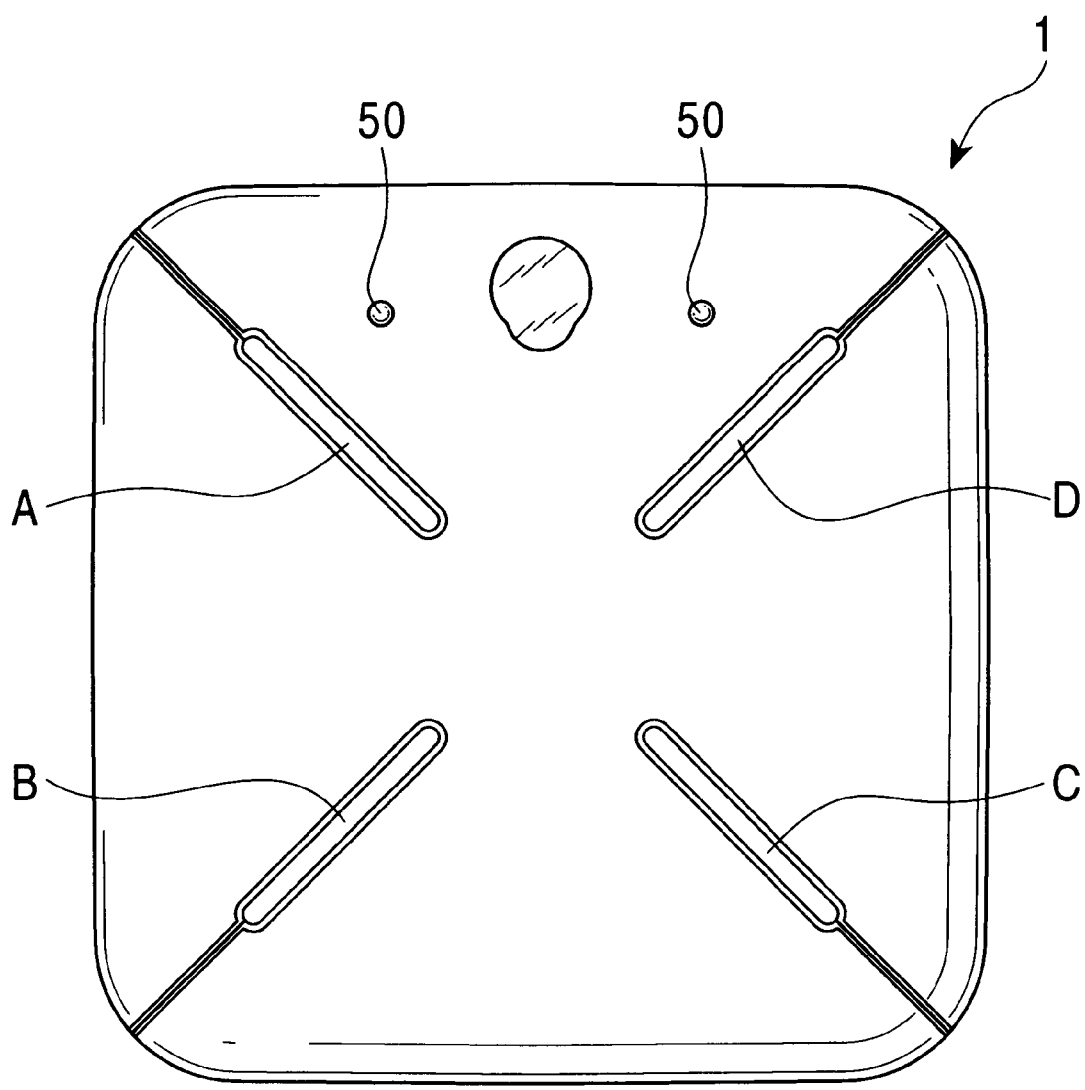
FIG. 10 is a plan view of a body fat scale showing a fifth embodiment of the present invention.

FIG. 10 shows a fifth embodiment. In addition to the construction of FIG. 1, this embodiment further includes a protrusion 50 as convex positioning means which is provided near each of the one pair of electrodes A and D serving as a current supply electrode at a position where toes are approximately located when an average subject steps on the measurement board 1 to bring his/her left foot sole into contact with the electrodes A and B and to bring his/her right foot sole into contact with the electrodes C and D.

When the average subject steps on the measurement board 1 to bring his/her left foot sole into contact with the electrodes A and B and to bring his/her right foot sole -into contact with the electrodes C and D, the subject adjusts to locate the portion of his/her foot soles contacting the protrusion 50 at the same position in every measurements. Thus, the foot soles contacts the electrodes at the same position all the time so that the influence of deviations in foot position on bioelectrical impedance can be prevented and thereby a precise measurement result can be obtained.

Further, a non-average subject, i.e. a subject having an extremely large foot size or an extremely small foot size, may position his/her toes outside or inside the protrusion 50 in every measurement. Thus, the foot soles contacts the electrodes at the same position all the time so that the influence of deviations in foot position on bioelectrical impedance can be prevented and thereby a precise measurement result can be obtained.

In the arrangement of the electrodes in FIGS. 6, 7 and 8, the above protrusion may also be provided. In these cases, the influence of deviations in foot position on bioelectrical impedance can also be prevented and thereby a precise measurement result can be obtained. When the protrusion is provided in the embodiment of FIGS. 6 or 8, all of subjects including subjects having extremely large foot size and extremely small foot size will adjust to locate the portion of their foot soles contacting the protrusion 50 at the same position in every measurements. When the protrusion is provided in the embodiment of FIG. 7, a subject having an extremely large foot size or an extremely small foot size will position his/her toes outside or inside the protrusion 50 in every measurement.

While the above embodiments have been describes-in conjunction with the body fat scale with the body weight scale, the present invention is not limited to such embodiments, and may apply to any bioelectrical impedance measuring apparatus, such as body fat scale, body water scale, or blood pressure and pulse meter.

According to one aspect of the present invention, since each of the four electrodes is formed to have an elongated shape and a small area and arranged to extend radially with respect to the center of the measurement board, any chilly feeling is not caused from foot soles superimposed on such electrodes, and an bioelectrical impedance can be adequately measured regardless of a foot size of a subject.

Further, by providing the positioning guide for positioning heels of a subject near and under of each of the electrodes, the influence of deviations in foot position can be prevented and thereby a accurate bioelectrical impedance measurement can be made.

According to another aspect of the present invention, since each of the four electrodes is formed to have an elongated shape and a small area and arranged to surround the center of the measurement board, any chilly feeling is not caused from foot soles superimposed on such electrodes, and an bioelectrical impedance can be adequately measured regardless of a foot size of a subject. Further, by providing the positioning guide for positioning heels of a subject near and under of each of the electrodes, the influence of deviations in foot position can be prevented and thereby a accurate bioelectrical impedance measurement can be made.

Further, by providing the convex positioning means near each of the electrodes serving as a current supply electrode, the measurement can be made at the same position all the time, and a precise measurement result can be obtained even if each of the applied electrodes has a small touch area.

What is claimed is:

1. A bioelectrical impedance measuring apparatus including a measurement board and two pairs of electrodes arranged on said measurement board, wherein a bioelectrical impedance of a subject is detected with bringing both foot soles of said subject into contact with said electrodes, characterized in that each of said two pairs of electrodes has an elongated shape and is arranged to extend approximately radially from the center of said measurement board.

2. A bioelectrical impedance measuring apparatus as defined in claim 1, wherein said two pairs of electrodes comprises a first pair of adjacent electrodes and a second pair of adjacent electrodes, wherein each of said first pair of adjacent electrodes serves as a current supply electrode, wherein the distance between respective lower portions of said first pair of adjacent electrodes is less than the distance between respective upper portions of said first pair of adjacent electrodes, and each of said second pair of adjacent electrodes serves as a voltage measuring electrode, wherein the distance between respective upper portions of said second pair of adjacent electrodes is less than the distance between respective lower portions of said second pair of adjacent electrodes.

3. A bioelectrical impedance measuring apparatus as defined in claim 2, which further includes positioning means for positioning a heel of said subject, said positioning means being located near each of said second pair of adjacent electrodes serving as a voltage measuring electrode.

4. A bioelectrical impedance measuring apparatus as defined according to claim 3, which further includes convex positioning means located near each of said first pair of adjacent electrodes serving as a current supply electrode.

5. A bioelectrical impedance measuring apparatus as defined according to claim 2, which further includes convex positioning means located near each of said first pair of adjacent electrodes serving as a current supply electrode.

6. A bioelectrical impedance measuring apparatus including a measurement board and two pairs of electrodes arranged on said measurement board, wherein a bioelectrical impedance of a subject is detected with bringing both foot soles of said subject into contact with said electrodes, characterized in that each of said two pairs of electrodes has an elongated shape and is arranged to surround the center of said measurement board, wherein said two pairs of electrodes comprises a first pair of adjacent electrodes and a second pair of adjacent electrodes, wherein each of said first pair of adjacent electrodes serves as a current supply electrode, wherein the distance between respective lower portions of said first pair of adjacent electrodes is greater than the distance between respective upper portions of said first pair of adjacent electrodes, and each of said second pair of adjacent electrodes serves as a voltage measuring electrode, wherein the distance between respective upper portions of said second pair of adjacent electrodes is greater than the distance between respective lower portions of said second pair of adjacent electrodes.

7. A bioelectrical impedance measuring apparatus as defined in claim 6, which further includes positioning means for positioning a heel of said subject, said positioning means being located near each of said second pair of adjacent electrodes serving as a voltage measuring electrode.

8. A bioelectrical impedance measuring apparatus as defined according to claim 7, which further includes convex positioning means located near each of said first pair of adjacent electrodes serving as a current supply electrode.

9. A bioelectrical impedance measuring apparatus as defined according to claim 6, which further includes convex positioning means located near each of said first pair of adjacent electrodes serving as a current supply electrode.

* * * * *